United States Patent [19]

Fontana

[11] Patent Number: 5,489,587
[45] Date of Patent: Feb. 6, 1996

[54] BENZOFURANS USED TO INHIBIT BONE LOSS

[75] Inventor: Steven A. Fontana, Martinsville, Ind.

[73] Assignee: Eli Lilly and Company, Indianapolis, Ind.

[21] Appl. No.: 376,955

[22] Filed: Jan. 20, 1995

[51] Int. Cl.$^6$ .............. A61K 31/535; A61K 31/445; A61K 31/40; A61K 31/36
[52] U.S. Cl. ............... 514/233.5; 514/320; 514/422; 514/465; 514/652
[58] Field of Search .................. 514/233.5, 320, 514/422, 465, 652

[56] References Cited

U.S. PATENT DOCUMENTS

| | | | |
|---|---|---|---|
| 5,254,594 | 10/1993 | Niikura et al. | 514/648 |
| 5,354,861 | 10/1994 | Sim et al. | 544/153 |
| 5,393,763 | 2/1995 | Black et al. | 514/333 |

*Primary Examiner*—T. J. Criares
*Attorney, Agent, or Firm*—Steven A. Fontana

[57] ABSTRACT

The present invention provides methods for inhibiting bone loss comprising administering to a mammal in need of treatment of a bone loss inhibiting amount of a compound of formula I

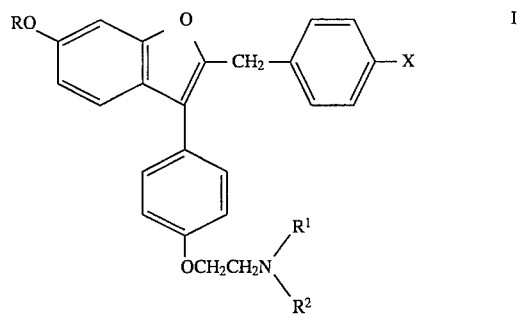

wherein
R is hydrogen or methyl;
$R^1$ and $R^2$ each are methyl or ethyl, or $R^1$ and $R^2$ together with the nitrogen atom to which they are attached represent a saturated heterocyclic group; and
X is bromo, chloro, fluoro, or hydrogen; or a pharmaceutically acceptable salt thereof.

15 Claims, No Drawings

BENZOFURANS USED TO INHIBIT BONE LOSS

BACKGROUND OF THE INVENTION

The present invention relates to the discovery that a group of benzofuran derivatives are useful for inhibiting bone loss in humans.

The mechanism of bone loss is not completely understood, but bone loss disorders arise from an imbalance in the formation of new healthy bone and the resorption of old bone, skewed toward a net loss of bone tissue. This bone loss involves a decrease in both mineral content and protein matrix components of the bone. Ultimately, such bone loss leads to an increased fracture rate of, predominantly, femoral bones and bones in the forearm and vertebrae. These fractures, in turn, lead to an increase in general morbidity, a marked loss of stature and mobility, and, in many cases, an increase in mortality resulting from complications.

Bone loss occurs in a wide range of subjects, including post-menopausal women, patients who have undergone hysterectomy, patients who are undergoing or have undergone long-term administration of corticosteroids, patients suffering from Cushing's syndrome, and patients having gonadal dysgenesis. The need for bone repair or replacement also arises locally in the case of bone fracture, non-union, defect, prosthesis implantation, and the like. Further, such need also arises in cases of systemic bone diseases, as in osteoporosis, osteoarthritis, Paget's disease, osteomalacia, osteohalisteresis, multiple myeloma and other forms of cancer and the like.

Unfortunately, there exists a need for effective pharmaceutical agents which would inhibit bone loss in mammals while having negligible or non-existent side effects.

SUMMARY OF THE INVENTION

The present invention provides a method for inhibiting bone loss comprising administering to a mammal in need of treatment a bone loss inhibiting amount of a compound of formula I

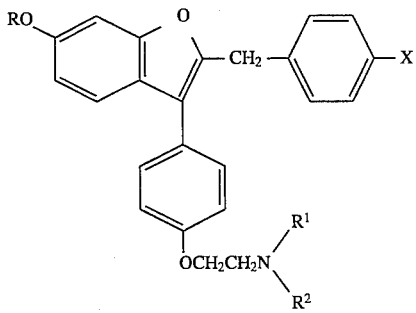

wherein

R is hydrogen or methyl;

$R^1$ and $R^2$ each are methyl or ethy, or $R^1$ and $R^2$ together with the nitrogen atom to which they are attached represent a saturated heterocyclic group; and X is bromo, chloro, fluoro, or hydrogen; or a pharmaceutically acceptable salt thereof.

DETAILED DESCRIPTION OF THE INVENTION

The present invention relates to methods for inhibiting bone loss comprising administering to a mammal in need of treatment a bone loss inhibiting amount of a compound of formula I

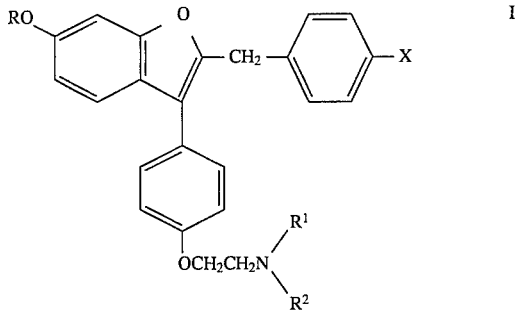

wherein

R is hydrogen or methyl;

$R^1$ and $R^2$ each are methyl or ethyl, or $R^1$ and $R^2$ together with the nitrogen atom to which they are attached represent a saturated heterocyclic group; and X is bromo, chloro, fluoro, or hydrogen; or a pharmaceutically acceptable salt thereof.

The present invention concerns the discovery that the compounds of formula I are useful for inhibiting bone loss. The methods of treatment provided by this invention can be practiced by administering to an animal, preferably a human, an amount that inhibits bone loss of a compound of formula I, or a pharmaceutically acceptable salt thereof. The methods include both medical therapeutic and/or prophylactic treatment, as appropriate. Generally, a formula I compound is formulated with common excipients, diluents or carriers, and put into capsules or compressed into tablets, or formulated as elixirs or solutions for convenient oral administration, or administered by the intramuscular or intravenous routes. The compounds may also be administered transdermally.

The methods of this invention also include the administration of a compound of formula I together with estrogen, either independently or in combination. The term estrogen as used herein refers to any compound which approximates the spectrum of activities of the naturally acting molecule which is commonly believed to be 17β-estradiol. Examples of such compounds include estriol, estrone, ethynyl estradiol, Premarin® (a commercial preparation of conjugated estrogens isolated from natural sources—Ayerst), and the like.

All of the compounds used in the methods of the present invention can be made according to established or analogous procedures, such as those detailed in U.S. Pat. No. 5,354,861, which is herein incorporated by reference. Modifications to these methods may be necessary to accommodate reactive functionalities of particular substituents. Such modifications would be either apparent to, or readily ascertained by, those skilled in the art.

Preferred formula I compounds are those in which $R^1$ and $R^2$ independently are methyl or ethyl or, when taken together with the nitrogensatom to which they are attached represent a pyrrolidino, piperidino, or morpholino group.

Representative preferred compounds are as follows:

2-(p-chlorobenzyl) -3-[p-(2-dimethylaminoethoxy) phenyl]-6-methoxy-benzo[b]furan;

2-(p-chlorobenzyl)-3-[p-(2-pyrrolidinoethoxy)phenyl] 6-methoxy-benzo[b]furan;

2-(D-chlorobenzyl)-3-[p-(2-piperidinoethoxy)phenyl]-6-methoxy-benzo[b]furan;

2-(1-chlorobenzyl)-3-[p-(2-morpholinoethoxy)phenyl]-6-methoxy-benzo[b]furan;

2-(p-fluorobenzyl)-3-[p-(2-dimethylaminoethoxy) phenyl]-6-methoxy-benzo[b]furan;

2- (p- fluorobenzyl) -3-[p-(2-pyrrolidinoethoxy)phenyl] 6-methoxy-benzoylfuran;

2-(p- fluorobenzyl)-3-[p-(2-piperidinoethoxy)phenyl]-6-methoxy-benzo[b]furan; and 2-(p-fluorobenzyl)-3-[p-(2-morpholinoethoxy)phenyl]-6-methoxy-benzo[b]furan.

The formula I compounds used in the methods of the present invention can form pharmaceutically acceptable acid addition salts with a variety of organic and inorganic acids and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne -1,4-dioate, hexyne-1,4-dioate, caprate, caprilate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenyl sulfonate, chlorobenzene-sulfonate, ethanesulfonate, 2-hydroxyethanesulfonate, methane-sulfonate, naphthalene-1-sulfonate, naphthalene-2-sulfonate, p-toluenesulfonate, xylenesulfonate, tartrate, and the like.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, a formula I compound, either alone or in combination with estrogen, can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinylpyrrolidone; moisturizing agents such as glycerol; disintegrating agents such as agaragar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

Compounds of formula I, either alone or in combination with estrogen, can also be formulated as elixirs or solutions for convenient oral administration or as solutions appropriate for parenteral administration, for instance by intramuscular, subcutaneous or intravenous routes. Additionally, the compounds, either alone or in combination with estrogen, can be formulated as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular dosage of a compound of formula I required to inhibit bone loss according to this invention will depend upon the severity of the condition, the route of administration, and related factors. In humans, generally accepted and effective daily doses will be from about 0.1 to about 1000 mg, and more typically from about 50 to about 600 mg. Such dosages will be administered to the patient from once to about three times each day, or more often as needed to inhibit bone loss effectively.

If estrogen is also administered, generally accepted and effective daily doses of estrogen will be from about 0.01 to about 4.0 mg, and more typically from about 0.1 to about 2.0 mg. These doses are also administered to the patient from once to about three times a day, or more often as needed.

For the purposes of this invention, the following are typical oral dosage forms. In these examples, "Active ingredient" means a compound of formula I.

Formulation 1:
Hard gelatin capsules are prepared using the following:

| Ingredient | Quantity (mg/capsule) |
|---|---|
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Tablets

The components in Formulation I can be blended and compressed to form tablets.

Alternatively, tablets each containing 0.1–1000 mg of active ingredient are made up as follows:

Formulation 2:

| Ingredient | Quantity (mg/tablet) |
|---|---|
| Active ingredient | 0.1–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve.

The sodium carboxymethyl starch, magnesium stearate, and talc, previously passed through a No. 60 U.S. sieve, are then added to the granules which, after mixing, are compressed on a tablet machine to yield tablets.

Suspensions

Suspensions each containing 0.1–1000 mg of medicament per 5 mL dose are made as follows:

Formulation 3:

| Ingredient | Quantity (amount/5 mL) |
|---|---|
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water | qs to 5 mL |

The medicament is passed through a No. 45 mesh U.S. sieve and mixed with the sodium carbolymethyl cellulose and syrup to form a smooth paste. The benzoic acid solution, flavor, and color are diluted with some of the water and added, with stirring. Sufficient water is then added to produce the required volume.

Formulation 4: Combination Capsule I

| Ingredient | Quantity (mg/capsule |
|---|---|
| Active ingredient | 50 |
| Premarin | 1 |
| Avicel pH 101 | 50 |
| Starch 1500 | 117.50 |
| Silicon Oil | 2 |
| Tween 80 | 0.50 |
| Cab-O-Sil | 0.25 |

Formulation 5: Combination Capsule II

| Ingredient | Quantity (mg/capsule |
|---|---|
| Active ingredient | 50 |
| Norethylnodrel | 5 |
| Avicel pH 101 | 82.50 |
| Starch 1500 | 90 |
| Silicon Oil | 2 |
| Tween 80 | 0.50 |

Formulation 6: Combination Tablet

| Ingredient | Quantity (mg/capsule) |
|---|---|
| Active ingredient | 50 |
| Premarin | 1 |
| Corn Starch NF | 50 |
| Povidone, K29–32 | 6 |
| Avicel pH 101 | 41.50 |
| Avicel pH 102 | 136.50 |
| Crospovidone XL10 | 2.50 |
| Magnesium Stearate | 0.50 |
| Cab-O-Sil | 0.50 |

The following nonlimiting test examples illustrate the methods of this invention.

Test Procedures

Six month old, female Sprague Dawley rats (weight range of 275 to 350 g; Harlan Sprague Dawley, Indianapolis, Ind.) are used in these studies. Ovariectomies (or a sham surgical procedure for controls) are performed by the vendor. The animals are shipped the day following surgery and housed in hanging wire cages. Room temperature is maintained at 22.2°± 1.7° C. with a minimum relative humidity of 40%. The photoperiod in the room is 12 hours light and 12 hours dark, with light onset at 0600. The animals have ad lib access to food (Teklad diet, TD 89222, 0.5% calcium, 0.4% phosphorus; Madison, Wis.) and water. The animals are allowed one day to acclimate to these conditions prior to experimental manipulation.

The test compound is suspended in 20% β-cyclodextrin (CDX). 20% CDX is used as the control vehicle. 17α-Ethynyl-estradiol (obtained from Sigma Chemical Co., St. Louis, Mo.) also is dissolved in 20% CDX, and is used as an internal standard for these studies.

On the third day post-ovariectomy, dosing with test compounds is initiated for prophylactic studies. For treatment studies, administration of the test compound is initiated about 20–35 days following the ovariectomy procedure. Oral gavages of 20% CDX, a compound of formula I (0.1 to 10 mg/kg), and/or 17α-ethynyl-estradiol(100 μg/kg) are delivered daily for 35 consecutive days. On the evening following the final dose, the animals are fasted. The animals are anesthetized with a mixture of Ketaset® and Rompun® (67 and 6.7 mg/kg, respectively) the next morning, and a 3-mL sample of blood is obtained by cardiac puncture. The animals are then asphyxiated with carbon dioxide, and body weight and uterine weight are recorded. The left femur is removed from each animal, cleaned and frozen for subsequent X-ray evaluation.

The distal end of the femur is x-rayed using a Norland NXR-1200 X-ray machine with a voltage of 47 kV and contrast at 4.5. Digitized X-ray images are transferred directly to a Macintosh computer station, and image analysis of the X-ray scan is conducted using the Ultimage® software program. Quantitation is achieved by measuring the total number of pixels in a standard region of interest proximal to the growth plate, over a gray scale range of zero to 60.

Experimental groups consist of 6 to 8 rats. Data for control and treated rats are compared by one way analysis of variance (ANOVA).

I claim:

1. A method for inhibiting bone loss comprising administering to a mammal in need of treatment a bone loss inhibiting amount of a compound of formula I

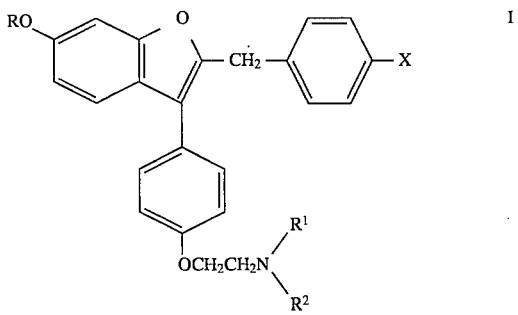

wherein

R is hydrogen or methyl;

$R^1$ and $R^2$ each are methyl or ethyl, or $R^1$ and $R^2$ together with the nitrogen atom to which they are attached represent a saturated heterocyclic group; and X is bromo, chloro, fluoro, or hydrogen; or a pharmaceutically acceptable salt thereof.

2. A method according to claim 1 wherein $R^1$ and $R^2$ of said formula I compound independently are methyl or ethyl, or together with the nitrogen atom to which they are attached represent a pyrrolidino, piperidino, or morpholino group.

3. A method according to claim 2 wherein said formula I compound is 2-(p-chlorobenzyl) -3- [p-(2-dimethylaminoethoxy) phenyl]-6-methoxy-benzo[b]furan.

4. A method according to claim 2 wherein said formula I compound is 2-(p-chlorobenzyl)-3-[p-(2-pyrrolidinoethoxy)phenyl] -6-methoxy-benzo[b]furan.

5. A method according to claim 2 wherein said formula I compound is 2-(p-chlorobenzyl)-3-[p-(2piperidinoethoxy)phenyl] -6-methoxy-benzo[b]furan.

6. A method according to claim 2 wherein said formula I compound is 2-(p-chlorobenzyl)-3-[p-(2morpholinoethoxy)phenyl] -6-methoxy-benzo[b]furan.

7. A method according to claim 2 wherein said formula I compound is 2-(p-fluorobenzyl)-3-[p-(2dimethylaminoethoxy phenyl]-6-methoxy-benzo[b]furan.

8. A method according to claim 2 wherein said formula I compound is 2-(p-fluorobenzyl)-3-[p-(2pyrrolidinoethoxy)phenyl] -6-methoxy-benzo[b]furan.

9. A method according to claim 2 wherein said formula I compound is 2-(p-fluorobenzyl)-3-[p-(2piperidinoethoxy)phenyl] -6-methoxy-benzo[b]furan.

10. A method according to claim 2 wherein said formula I compound is 2-(p-fluorobenzyl-3-[p-(2morpholinoethoxy)phenyl] -6-methoxy-benzo[b]furan.

11. A method for inhibiting bone loss comprising the method of claim 1, and further comprising administering to said mammal an effective amount of estrogen.

12. A method according to claim 1 wherein said mammal is a human.

13. A method according to claim 12 wherein said human is a female.

14. A method according to claim 11 wherein said mammal is a human.

15. A method according to claim 14 wherein said human is a female.

* * * * *